Figure 1:
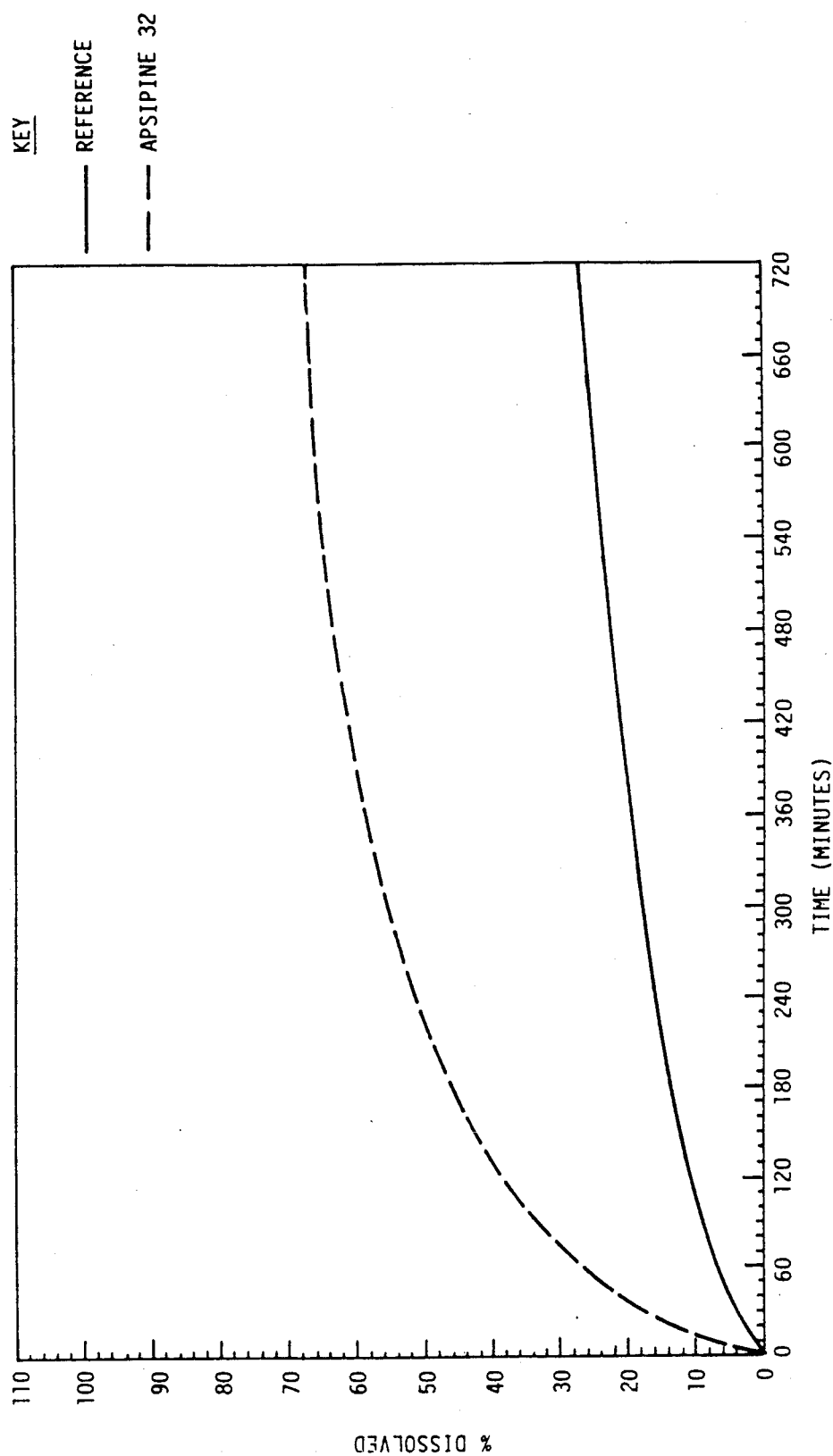

United States Patent [19]
Barry et al.

[11] Patent Number: 5,051,263
[45] Date of Patent: Sep. 24, 1991

[54] CONTROLLED-RELEASE FORMULATIONS

[76] Inventors: Brian W. Barry, 23 Dales Way, Tranmere Park, Guiseley, Leeds LS20 8JN; Bryan Arthur Mulley, 10 Yew Tree Avenue, Bradford, West Yorkshire BD 8 0AD; Peter York, 24 Parish Ghyll Rd., Ilkley, Yorkshire, all of Great Britain

[21] Appl. No.: 256,791

[22] Filed: Oct. 12, 1988

[30] Foreign Application Priority Data

Oct. 12, 1987 [GB] United Kingdom ............... 8723896

[51] Int. Cl.⁵ .................................... A61K 9/16
[52] U.S. Cl. ........................ 424/490; 424/489; 424/488; 424/487; 424/451
[58] Field of Search .............. 424/490, 488, 489, 487

[56] References Cited

U.S. PATENT DOCUMENTS

| | | | |
|---|---|---|---|
| 4,309,404 | 1/1982 | DeNeale et al. | 424/489 |
| 4,723,957 | 2/1988 | Magruder et al. | 424/487 |
| 4,777,033 | 10/1988 | Ikura et al. | 424/488 |
| 4,808,413 | 2/1989 | Joshi et al. | 424/489 |

FOREIGN PATENT DOCUMENTS 0232155 8/1987 European Pat. Off.

*Primary Examiner*—Thurman Page
*Assistant Examiner*—William E. Benston, Jr.

[57] ABSTRACT

A controlled-release formulation of a pharmacologically active substance of poor aqueous solubility comprising sufficient granules to provide a predetermined dose or number of doses of the pharmacologically active substance, each of said granules comprising 100 parts of said pharmacologically active substance and usually from 20 to 400 parts of carbomer.

The granules are optionally each provided with a coating covering substantially the whole surface thereof and comprising 100 parts of water insoluble but water swellable acrylic polymer and from 20 to 70 parts of a water soluble hydroxylated cellulose derivative, the weight of the underlying granule and the diameter of the coated granules being between 0.5 and 2.5 mm.

A method for preparing the formulation is also provided.

11 Claims, 11 Drawing Sheets

DISSOLUTION CURVES FOR NIFEDIPINE SUSTAINED-RELEASE BEADS (a) AND ADALAT RETARD TABLETS (b)

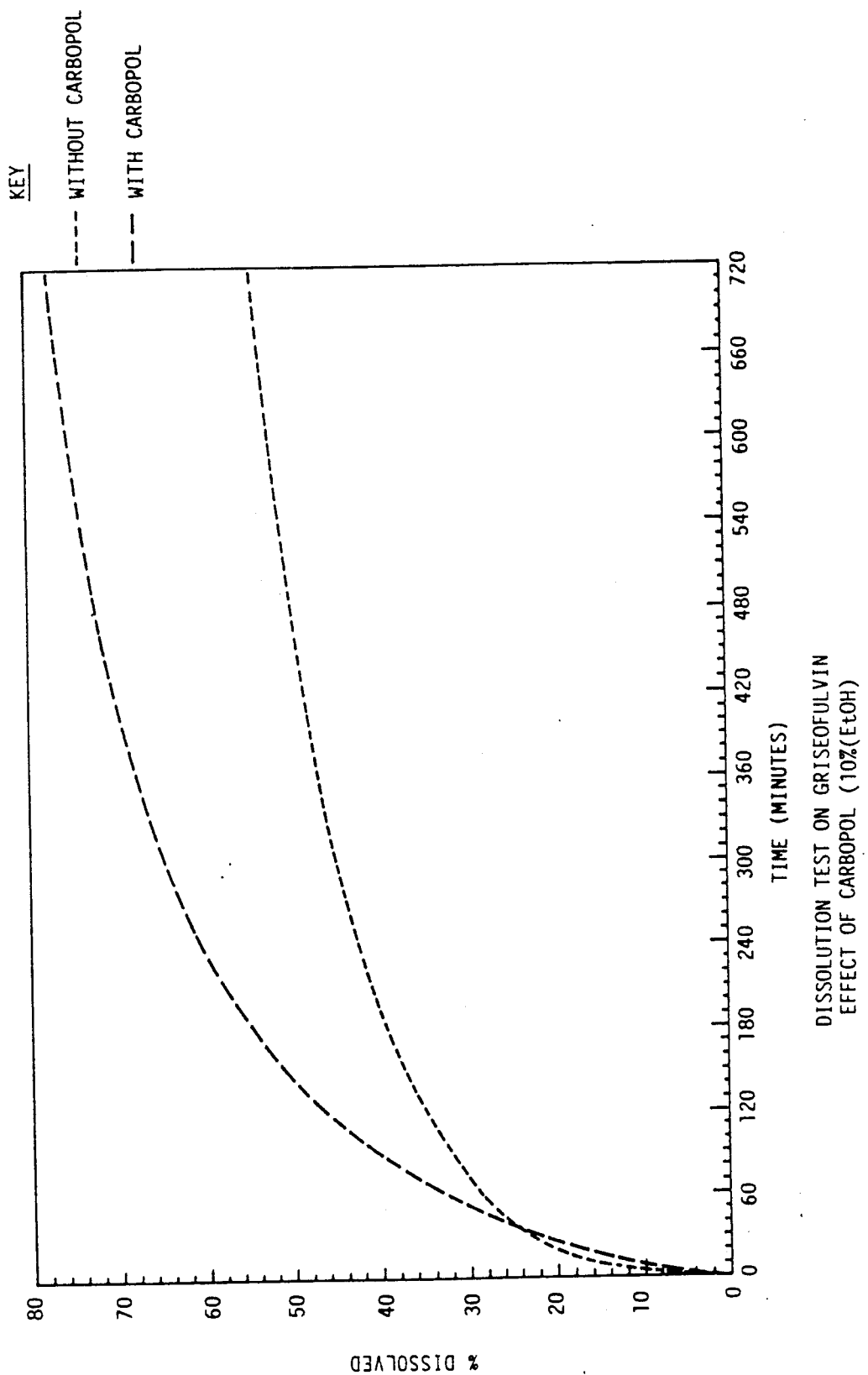

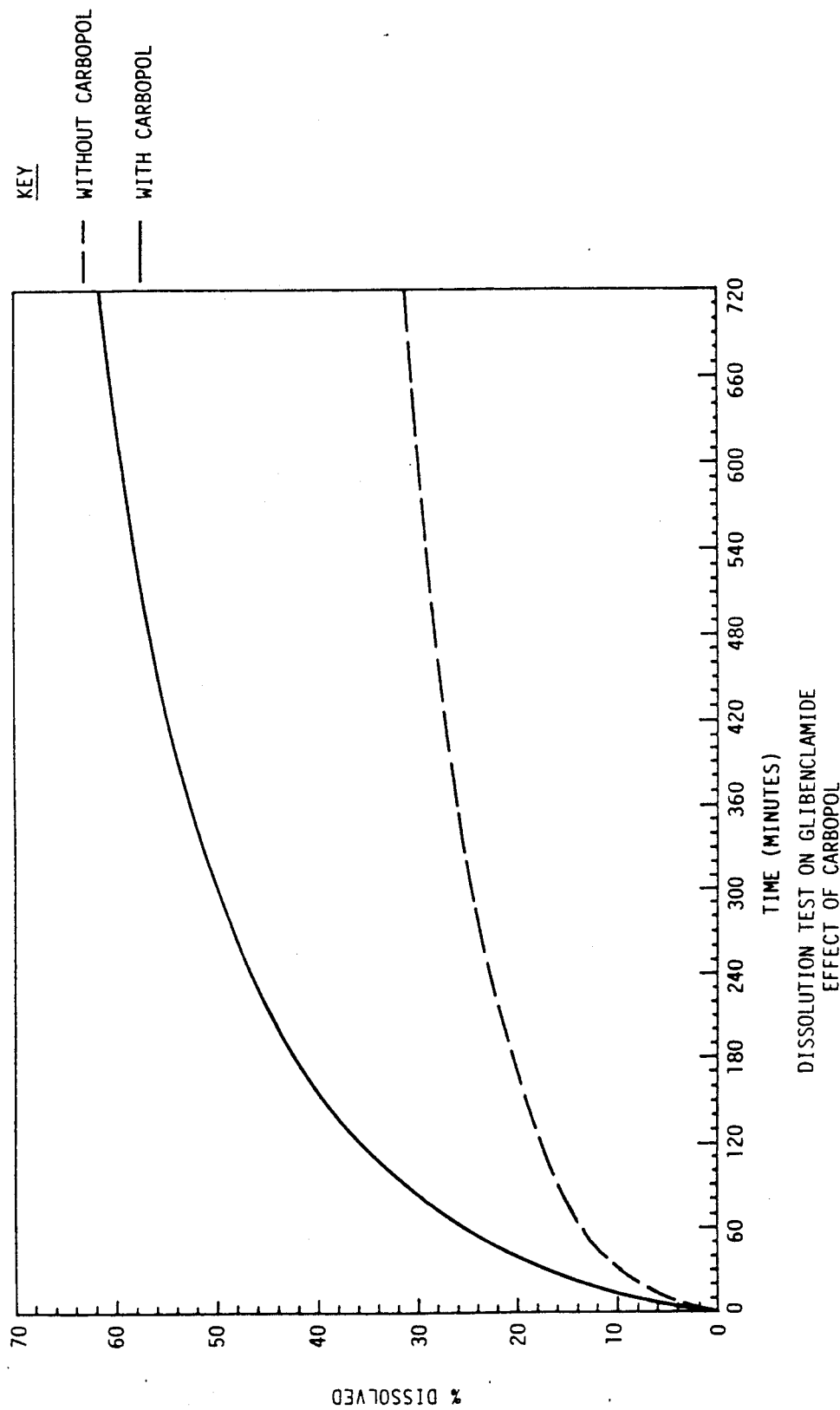

CONTROLLED-RELEASE FORMULATIONS

This invention relates to controlled-release formulations containing a pharmacologically active substance of poor aqueous solubility and, most preferably, to such formulations which will provide a combination of fast dissolution and sustained-release of the active ingredient over a period of about twelve or twenty-four hours. A method for preparing the controlled-release formulations is also provided.

Some medical conditions are best treated by administration of a pharmaceutical which is formulated to allow the active substance or ingredient to act as quickly as possible. Such a formulation may comprise an injectable solution or a readily dissolvable tablet or capsule. This type of formulation is useful, for instance, for treating acute pain, such as headaches, or pain associated with sudden trauma, such as an accident.

Other medical conditions are best treated by administration of a pharmaceutical in such a way as to sustain its action over an extended period of time. This type of administration is useful, for example, for treating chronic pain, such as that associated with rheumatic or arthritic conditions, or for the treatment of a chronic cardiovascular condition. It can be achieved by repeated administration of an immediate-release tablet or capsule at frequent intervals, for instance every four hours. However, this is generally inconvenient, especially during the night, when it is often necessary to awaken a patient to administer the tablet or capsule. In addition, such multiple dosing may lead to undesirable fluctuations in the plasma concentration of the active substance.

It has previously been proposed to produce a formulation which will release the active substance therein at a controlled rate such that the amount available in the body to treat the condition is maintained at a relatively constant level over an extended period of time. Particularly suitable periods are twelve hours and twenty-four hours, since such formulations need only be taken once or twice a day to maintain an effective treatment of the condition. Such formulations are generally known as "sustained-release formulations."

Many sustained-release formulations are already known, but there is no generally applicable method by which such formulations can be designed. Each formulation is dependent on the particular active substance incorporated therein. In designing a formulation, it is generally necessary to take into account many factors, including the rates of absorption and clearance of the active substance, the interaction of the active substance with the excipients and/or coatings to be used in the formulation, the solubility of the active substance and of the excipients and/or coatings, and the effects on the bioavailability of the active substance which may be caused by the excipients and/or coatings. It is, however, not possible readily to predict whether any particular formulation will provide the desired sustained-release, and it is generally found necessary to carry out considerable experimentation to produce a sustained-release formulation having the desired properties.

Additional problems arise when the pharmacologically active substance to be administered is poorly soluble in water and other aqueous solutions. Such substances, which include some of the most useful and widely prescribed pharmaceuticals, are notoriously difficult to formulate effectively for oral administration.

Nifedipine is the generic name for 4-(2'-nitrophenyl)-2,6-dimethyl-3,5-dicarbomethoxy-1,4-dihydropyridine. It is a vasodilator known to be useful for the treatment of hypertension and angina pectoris. Nifedipine is practically insoluble in water and has proved difficult to formulate effectively for oral administration. British Patent No. 1,173,862 relates to nifedipine itself and describes preparations thereof, optionally in admixture with an inert liquid or solid diluent or carrier, in the form of tablets and pills. These preparations have the disadvantage of a very slow and unpredictable rate of absorption from the gastrointestinal tract.

U.S. Pat. No. 3,784,684 describes oral-release capsules which are prepared by dissolving nifedipine using a solubilising agent and enclosing the solution in a capsule. The capsule provide a very rapid release of the nifedipine in a form which is readily absorbable by the body. However, liquid preparations in capsules are more inconvenient to produce than solid preparations. Further, because of the low solubility of nifedipine, a large amount of the solubilising agent is required and so the unit doses, and thus the capsules containing them, are usually large. This is obviously a disadvantage with preparations intended for oral administration.

European Patent Application No. 0001247 relates to pharmaceutical preparations for oral administration which comprise either a solution of nifedipine in polyethylene glycol or a non-crystalline dispersion of nifedipine in polyvinylpyrrolidone. These preparations are said to be stable and to present nifedipine in a form which is easily and rapidly absorbable by the body.

British Patent No. 1,579,818 describes various solid pharmaceutical preparations containing nifedipine. These include preparations which comprise a mixture of nifedipine and one or more of methyl cellulose, hydroxypropyl cellulose and hydroxypropylmethyl cellulose, optionally together with other components. The preparations are produced by a method which involves dissolving the ingredients in an organic solvent, which is then extracted leaving a solid composition or a powdery solid composition. The resulting preparations show a rapid release of the nifedipine and are said to show the same high bioavailability within the body as the previously mentioned liquid preparations. There is no teaching or suggestion that the preparations could be formulated with a coating for achieving sustained-release properties.

Carbomer is the generic name for carboxypolymethylene. It is a polymer of acrylic acid cross-linked with allylsucrose and has the following structure:

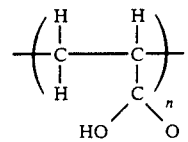

Carbomer is widely used in the manufacture of cosmetics and in various industrial suspensions and emulsions. It is water soluble and is used as a gelling agent and as a suspending agent in pharmaceutical preparations for internal and external use. Carbomer is employed as an emulsifying agent in the preparation of oil-in-water emulsions for external use and is effective as a thickener in ointments and creams. It is also known for use as a binding agent in tablets and there has been some suggestion in the literature that it could be used in the preparation of sustained-release formulations. However, carbomer is more commonly used in pharmaceutical liquid and semi-solid dosage forms than in tablets.

As previously mentioned, a major problem with formulating drugs like nifedipine is their low solubility. The present inventors have surprisingly discovered that the presence of carbomer in a suitable amount improves the solubility of such poorly soluble drugs and assists in the dissolution of controlled-release formulations. It is acknowledged above that carbomer has previously been suggested for inclusion in sustained-release formulations, but this use has only been to take advantage of its properties as a binder or thickening agent. Heretofore, the viscosity enhancing effect of carbomer has been regarded as a means to achieve a reduction in the release rate of the active ingredient in the sustained-release formulation. References include Choulis, N. H. and Papadopoulos, H. (1975). J. Pharm Sci., 64, 1033-1035 and Baun, D. C. and Walker, G. C. (1971). Pharm. Acta. Helv., 46, 94-113. As such, carbomer would clearly only be considered appropriate for use with pharmacologically active substances that are readily soluble. However, the present inventors believe that carbomer has rarely, if ever, actually been used in any marketed oral sustained-release capsule or tablet formulation and they are aware of no such formulations currently on the U.K. market. The present discovery that the presence of carbomer can increase the rate of dissolution of poorly soluble substances is the complete opposite of its previously suggested use in sustained-release formulations and is both surprising and advantageous.

With regard to the aforementioned nifedipine, a fast release formulation containing this drug is currently marketed in the United Kingdom under the name Adalat (a registered trade mark). This is in the form of a liquid held within gelatin capsules. A sustained-release formulation containing nifedipine is currently marketed under the name Adalat Retard (a registered trade mark). However, this formulation does not provide as good a sustained-release as is desirable. There is therefore a need for a controlled-release nifedipine formulation which combines fast dissolution and improved sustained-release, particularly over a period of twelve or twenty-four hours. The present invention seeks to provide such a controlled-release formulation. There is similarly a need for improved formulations of other pharmacologically active substances of poor aqueous solubility.

According to the present invention there is provided a controlled-release formulation of a pharmacologically active substance of poor aqueous solubility comprising sufficient granules to provide a predetermined dose or number of doses of the pharmacologically active substance, each of said granules comprising 100 parts of said pharmacologically active substance and at least 20 parts of carbomer.

In one embodiment of the invention, each of the aforesaid granules is provided with a coating covering substantially the whole surface thereof and comprising 100 parts of a water insoluble but water swellable acrylic polymer and from 20 to 70 parts of a water soluble hydroxylated cellulose derivative, the weight of the coating being from 2 to 25% of the weight of the underlying granule and the diameter of the coated granules being between 0.5 and 2.5 mm.

The invention further provides a method for preparing these controlled-release formulations and which comprises:
i) mixing the pharmacologically active substance with carbomer;
ii) forming the mixture into granules comprising 100 parts of the pharmacologically active substance and at least 20 parts of carbomer; and optionally
iii) forming a suspension comprising 100 parts of a water insoluble but water swellable acrylic polymer and from 20 to 70 parts of a water soluble hydroxylated cellulose derivative; and
iv) coating the said granules with the said suspension to form coated granules having a diameter of between 0.5 and 2.5 mm.

In the following description, all parts and percentages are by weight unless otherwise indicated.

It will be appreciated that the precise diameter and composition of the granules comprising the pharmacologically active substance and carbomer will depend on the time over which the formulation is designed to work. Generally, however, each of the granules will have a diameter of between 0.5 and 2.5 mm, preferably between 0.7 and 1.2 mm. For every 100 parts of the active ingredient present there will be from 20 to 400 parts, preferably 100 to 300 parts, of carbomer.

Turning now to the embodiment wherein the granules are coated, to some extent the diameter of the coated granules, the composition of the granules themselves and the composition and amount of coating will each depend on the time over which the formulation is designed to work. Generally, however, each of the coated granules will have a diameter of between 0.5 and 2.5 mm, preferably between 0.7 and 1.2 mm. For every 100 parts of the pharmacologically active substance present in the granule, there will generally be from 20 to 400 parts of carbomer, preferably 100 to 300 parts. For very potent pharmacologically active substances administered in dosages of less than a few milligrams, e.g. digoxin and digitoxin, more than 400 parts of carbomer may be used before processing difficulties arise. For every 100 parts of the water insoluble but water swellable acrylic polymer present in the coating, there will be from 20 to 70 parts of the water soluble hydroxylated cellulose derivative. The weight of the coating will usually be from 2 to 25% of the weight of the underlying granule.

For a formulation of, for example, nifedipine designed to provide controlled-release over a period of twelve hour, the coated granule diameter is generally between 0.7 and 1.2 mm, the granules preferably contain from 100 to 300 part of carbomer, and most preferably equal parts by weight of the active ingredient and carbomer, the coating preferably contains from 20 to 40 parts of the water soluble hydroxylated cellulose derivative, and the weight of the coating is between 2 and 10% of the weight of the underlying granule.

The formulations can, of course, be designed to provide controlled-release over longer or shorter periods of time, for example a twenty-four hour period.

The formulations of this invention may contain any pharmacologically active substance which is essentially insoluble or only poorly soluble in water or other aqueous solutions. Examples include: nifedipine, spironolactone (a diuretic), griseofulvin (an antibiotic/antifungal agent) and glibenclamide (an antidiabetic agent). Further examples include: bishydroxycoumarin, chloramphenicol, dapsone, digitoxin, digoxin, ergotamine, erythromycin, erythromycin stearate, nitrofurantoin, tolbutamide and steroids for example cortisone, methylprednisolone, prednisone, prednisolone and stilboestrol.

In addition to the pharmacologically active substance and carbomer, the formulations also preferably contain a bulking agent such as microcrystalline cellulose. This is a well known form of cellulose which is partially depolymerised. A particularly suitable microcrystalline cellulose is sold under the name Avicel (a registered trade mark). However, other conventional bulking agents may also be used, as will be readily apparent to those skilled in the art.

The formulations may also contain a diluent, such as lactose. A capillary-active agent, such as sodium carboxymethylcellulose, which is sold under the name Ac-Di-Sol (a registered trade mark), may additionally be included. These components are used in conventional amounts. If desired, the formulations of this invention may also contain colouring agents, sweetening agents and flavouring agents.

Carbomer contains a large proportion of carboxyl groups and it is these which gave rise to its previously known use as a thickening agent. However, extensive gelling can be undesirable in controlled-release formulations and it may be necessary to restrict temporarily the ionisation of the carboxyl groups. This can be achieved by increasing the ionic strength of the formulation, for example by including sodium chloride (typically in an amount of from 15 to 30% by weight). Alternatively, the environment of the carboxyl groups may be altered by including small amounts of, for example, citric acid, tartaric acid or fumaric acid (or their salts) in the formulation. They may be added either in solution or in solid form and typically in an amount of from 5 to 15%. The same effect may be achieved by adding other similar acids or salts thereof, as will be readily apparent to those skilled in the art. The addition of tri-sodium citrate to the formulation is particularly preferred.

The coating, when present, preferably comprises about 30 parts of the hydroxylated cellulose derivative. If too much is present, the coating may become too sticky and the rate of release may become too high. If too little is present, the rate of release may be too low. A particularly suitable hydroxylated cellulose derivative is hydroxypropylmethyl cellulose having a degree of substitution of 28 to 30% of methoxy groups and 7 to 12% of hydroxy groups. However, other equivalent materials such as hydroxypropyl, hydroxyethyl or hydroxymethyl celluloses can be used.

The acrylic polymer component of the coating is preferably neutral and may comprise a homopolymer or a copolymer, for instance of acrylic acid esters or methacrylic acid esters. Preferably, the acrylic polymer is provided as an aqueous dispersion. A particularly suitable acrylic polymer is sold under the name Eudragit (a registered trade mark), which comprises a copolymer of acrylic and methacrylic acid esters and which is usually supplied as an aqueous dispersion containing approximately 30% solids.

The formulations of this invention can be prepared in the following manner. The pharmacologically active substance, e.g. nifedipine, is micronised (to increase its surface area and thereby improve dissolution) and then blended with the carbomer and any other constituents, such as a bulking agent, a diluent and a capillary-active agent. Alternatively, the active ingredient and the carbomer may be mixed and then micronised, prior to blending with the other constituents. The blending is conveniently performed by mixing the components in a dry blender. If desired, sodium chloride, tri-sodium citrate or citric acid (or other acid or salts thereof) may then be added. Some water is next added to produce a slightly cohesive product. This is then extruded, chopped into suitable lengths, spheronised and dried to produce the formulation of the invention.

In an alternative method of preparation, the pharmacologically active substance and carbomer are co-precipitated from ethanol or other suitable solvent onto a microcrystalline cellulose base.

In the case of the coated formulation, the coating is prepared by forming a solution of the hydroxylated cellulose derivative and mixing it with a dispersion of the acrylic polymer. The aqueous mixture is then used to coat the dried granules, prepared as described above, and these are subsequently dried to produce coated granules. Preferably, the coated granules are then sieved to ensure that they are in the correct size range.

The resulting formulations of this invention may be supplied loose with a means for dispensing a measured amount, for instance to be sprinkled on food. Alternatively, they may be provided in sachets containing measured amounts. More preferably, however, the formulations are placed in measured amounts in readily soluble capsules. The capsule may be any of those already known in the art, and may, for instance, comprise a thin gelatin skin. Preferably, the capsule contains a sufficient amount to provide a conventional dose of the pharmacologically active substance (e.g. 10, 20 or 40 mg of nifedipine). The granules may, if desired, be formed into tablets using conventional tabletting machinery. If a coating is present, however, it should be recognised that normal tabletting processes would be likely to damage at least some of the coated granules.

It has surprisingly been found that by the above set out selection of materials and the relative amounts thereof, it is possible to produce controlled-release formulations which show effective controlled-release of the active ingredient over any desired period and, in particular, over a twelve hour period. The presence of carbomer in an amount within the ranges indicated above leads to controlled-release formulations which combine both fast dissolution and sustained-release properties. The formulations of this invention generally show quick dissolution within the granule, good sustained-release and improved total release of the active ingredient. The precise release characteristics shown by the formulations can, of course, be altered by varying the proportion of carbomer present, the presence and composition of a coating, and by the addition or deletion of the other components mentioned previously.

It has been found that the presence of carbomer promotes the dissolution of otherwise poorly soluble pharmacologically active substances. If used alone, drugs of this type would be released only very slowly, because dissolution into body fluids is a prerequisite for absorption into the blood stream. Since it has been found that the inclusion of carbomer promotes dissolution, a mixture of carbomer with a poorly soluble drug might achieve a near ideal release profile without any coating. It is therefore considered that carbomer can also be used to promote the immediate release of poorly soluble pharmacologically active substances, although judicious choice of the ratio of active ingredient: carbomer can achieve a sustained-release formulation even without a coating. Immediate or fast release formulations containing carbomer and a pharmacologically active substance of poor aqueous solubility are thus within the scope of this invention. The term "controlled-release formulation" as used herein is to be understood to refer to any formulation having a predetermined release profile (i.e. immediate, fast or sustained-release).

In view of the previously suggested use of carbomer in sustained-release formulations as a binding or thickening agent, it is considered most surprising that it has now been found that the presence of certain proportions of carbomer will improve the solubility of otherwise poorly soluble pharmacologically active substances. The mechanism by which carbomer achieves this dissolution enhancement is not fully known. However, an appropriate mixture of the active ingredient and carbomer produces a formulation which most advantageously has both good fast dissolution and sustained-release characteristics. A polymeric coating, when present, further enhances the sustained-release properties of the formulation and this can of course be designed to achieve the desired release characteristics. Before the coating can exert its delaying effect on the release of the drug, the drug itself must go into solution inside the granules and this is the effect surprisingly promoted by the presence of carbomer.

The present invention will now be illustrated by the following Examples. The Examples are by way of illustration only; they do not necessarily represent fully optimised formulations. The formulations described below were developed using the OSAT system developed by the inventors at the University of Bradford. The Examples refer to the use of Carbopol 934 and Carbopol 934 P which are commercially available brands of carbomer. (Carbopol is a registered trade mark). The dissolution test used in all cases was the USP basket method. The dissolution profiles obtained for the various formulations are shown in the accompanying FIGS. 1 to 11.

EXAMPLE 1

A formulation according to the present invention (designated Apsipine 32) was prepared from the following components:
10% micronized nifedipine
10% Carbopol 934 P
80% Avicel PH101
with distilled water to bind.
Micronised nifedipine and the Carbopol and Avicel were mixed together in a dry blender. Water was added in portions until a slightly cohesive product was formed. The cohesive product was passed through an extruder and the extruded material was chopped to produce slugs having a diameter of about 1 mm and a length of 2 to 3 mm. The slugs were spheronised by passage through a spheroniser, and the granules thus formed were dried to constant weight. A reference formulation was prepared in a similar manner for comparative purposes, but with the 10% Carbopol replaced by 10% lactose.

The dissolution test used (in each of Examples 1 to 7) was the USP basket method, pH 6.8, flat-bottomed flask, temperature of 37° C., detector wavelength 238 nm, optical density of 3 mg/l nifedipine solution was 0.171.

Dissolution tests were performed on samples of granules of both formulations and the results are shown in FIG. 1. The formulation of the present invention (Apsipine 32) gave good release for 3-4 hours after which time the release rate slowed considerably to give a 60-70% release after 12 hours.

EXAMPLE 2

The formulations of Example 1 were prepared as before but this time also containing 23% by weight of sodium chloride in order to limit gel formation by the carbomer. Dissolution tests were performed and the resulting dissolution profiles showed slight differences to those appearing in FIG. 1.

EXAMPLE 3

A formulation according to the present invention (designated Apsipine 37) was prepared from the following components:
10% micronized nifedipine
5% Carbopol 934
10% tri-sodium citrate
15% lactose
60% Avicel PH101
with distilled water to bind.
The formulation was prepared according to the method described in Example 1, the tri-sodium citrate and the lactose being added to the blender. A reference formulation was prepared as in Example 1 for comparative purposes.

Figure 2:
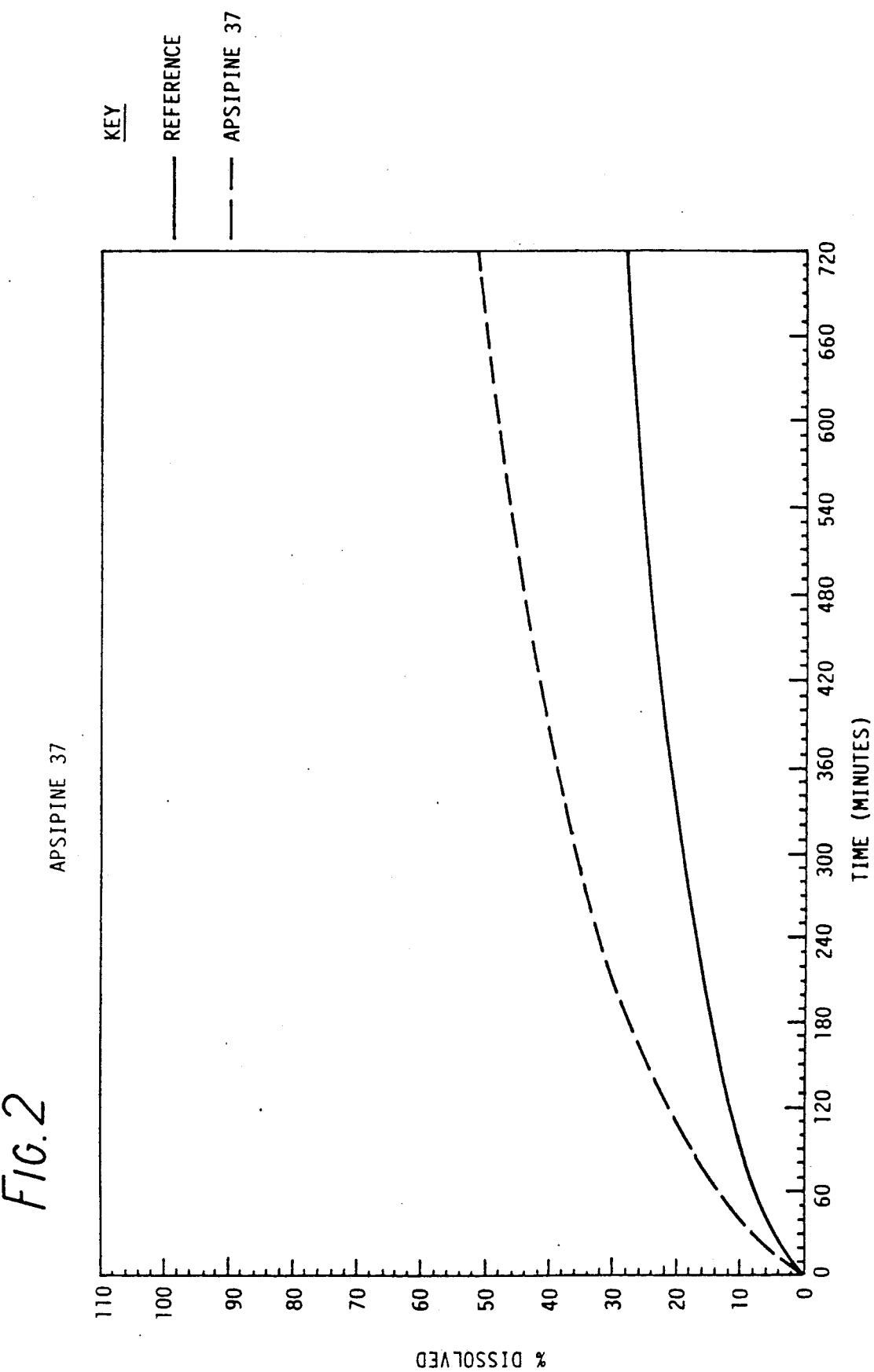

Dissolution tests were performed on samples of granules of both formulations and the results are shown in FIG. 2. These show that the granules of the formulation of the present invention (Apsipine 37) gave an approximately 50% release after 12 hours.

EXAMPLE 4

A formulation according to the present invention (designated Apsipine 39) was prepared from the following components:
10% micronized nifedipine
10% Carbopol 934
5% tri-sodium citrate
15% lactose
60% Avicel PH 101
with distilled water to bind.
The formulation was prepared according to the method described in Example 1, except that the nifedipine and the Carbopol were micronised together before being blended with the other components. A reference formulation was prepared as in Example 1 for comparative purposes.

Figure 3:
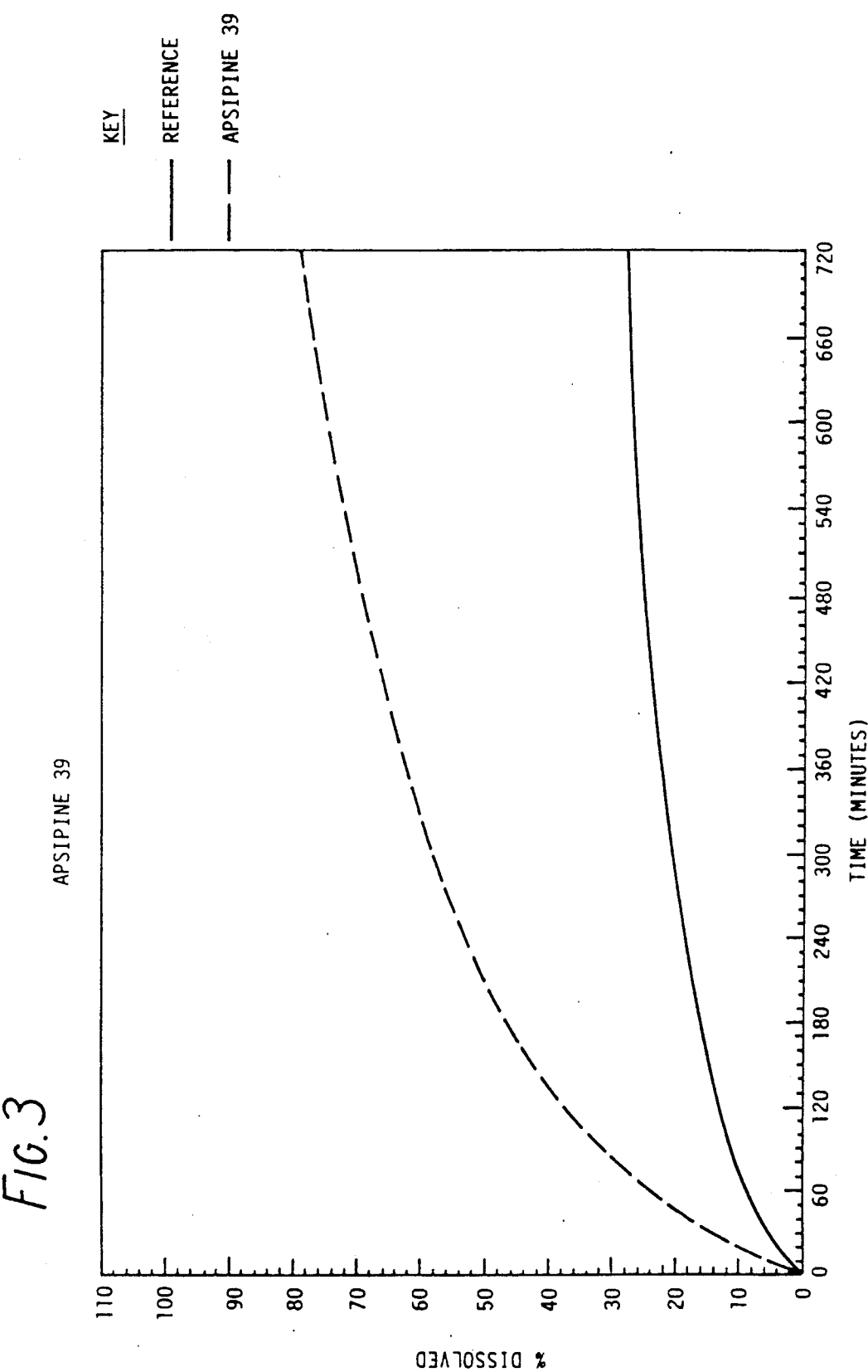

Dissolution tests were performed on samples of granules of both formulations and the results are shown in FIG. 3. These show that the granules of the formulation of the present invention (Apsiphine 39) gave 80% release after 12 hours and a good release profile.

EXAMPLE 5

Example 4 was repeated, but the tri-sodium citrate was replaced by citric acid which was then dissolved in the distilled water before being added to the blended powders. The resulting formulation of the present invention was designated Apsipine 42. A reference formulation was prepared as in Example 1 for comparative purposes.

Figure 4:
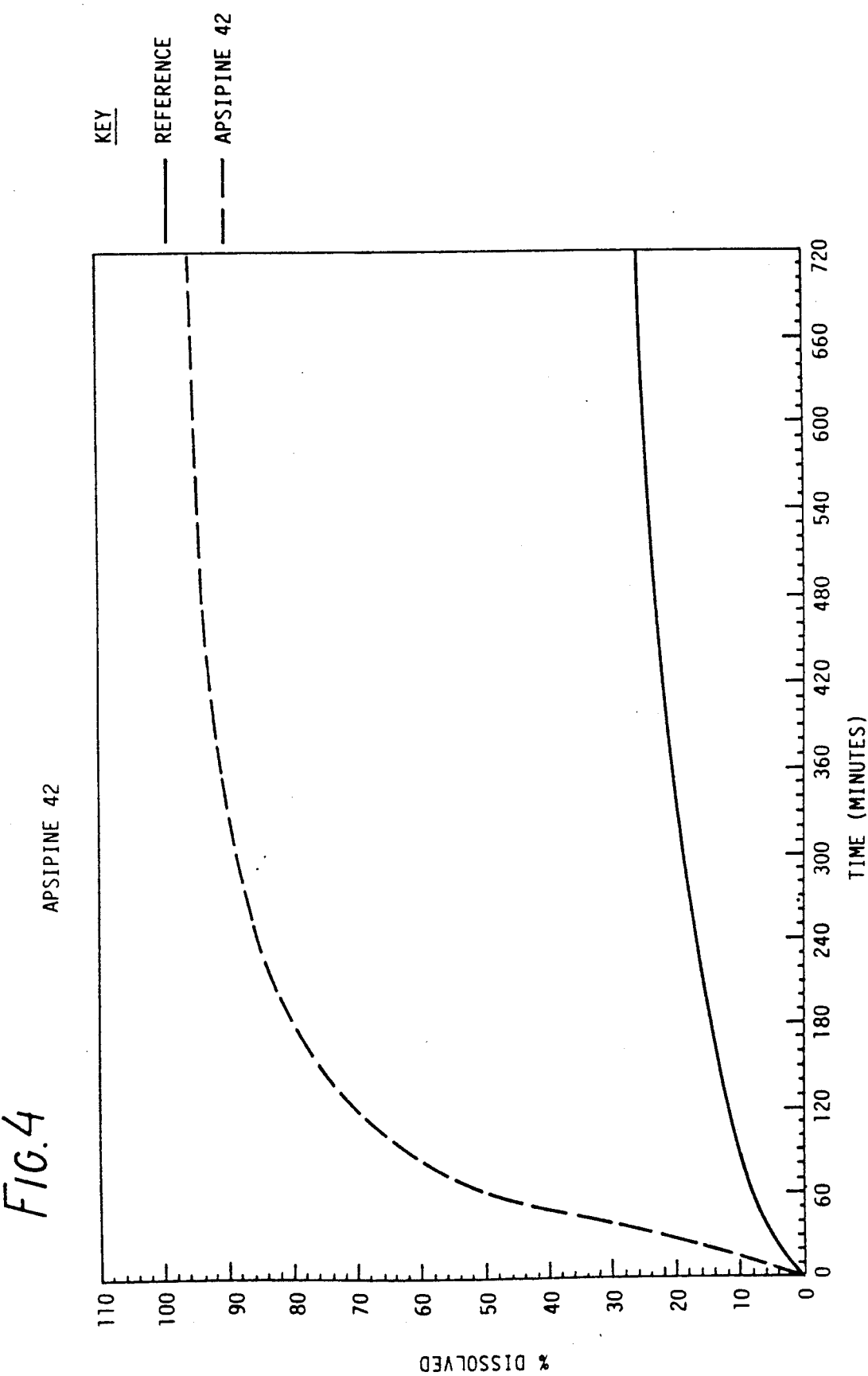

Dissolution tests were performed on samples of granules of both formulations and the results are shown in FIG. 4. The dissolution profile of the granules of the formulation of the present invention (Apsipine 42) was speeded up still further. 70% of the nifedipine in this formulation was released in 2 hours with nearly 90% being released after 6 hours.

EXAMPLE 6

Two identical formulations according to the present invention (designated Apsipine 44 and Apsipine 45) were prepared from the following components:
7% nifedipine
14% Carbopol 934
59% Avicel PH 101
17.5% lactose
2.5% citric acid
with distilled water to bind.
The formulations were prepared according to the method described in Example 1 except that the nifedipine and the Carbopol were micronised together before being blended with the other components and that in one formulation the citric acid was dissolved in the distilled water, this solution being used to bind the remaining powders together. A reference formulation was prepared as in Example 1 for comparative purposes.

Figure 5:
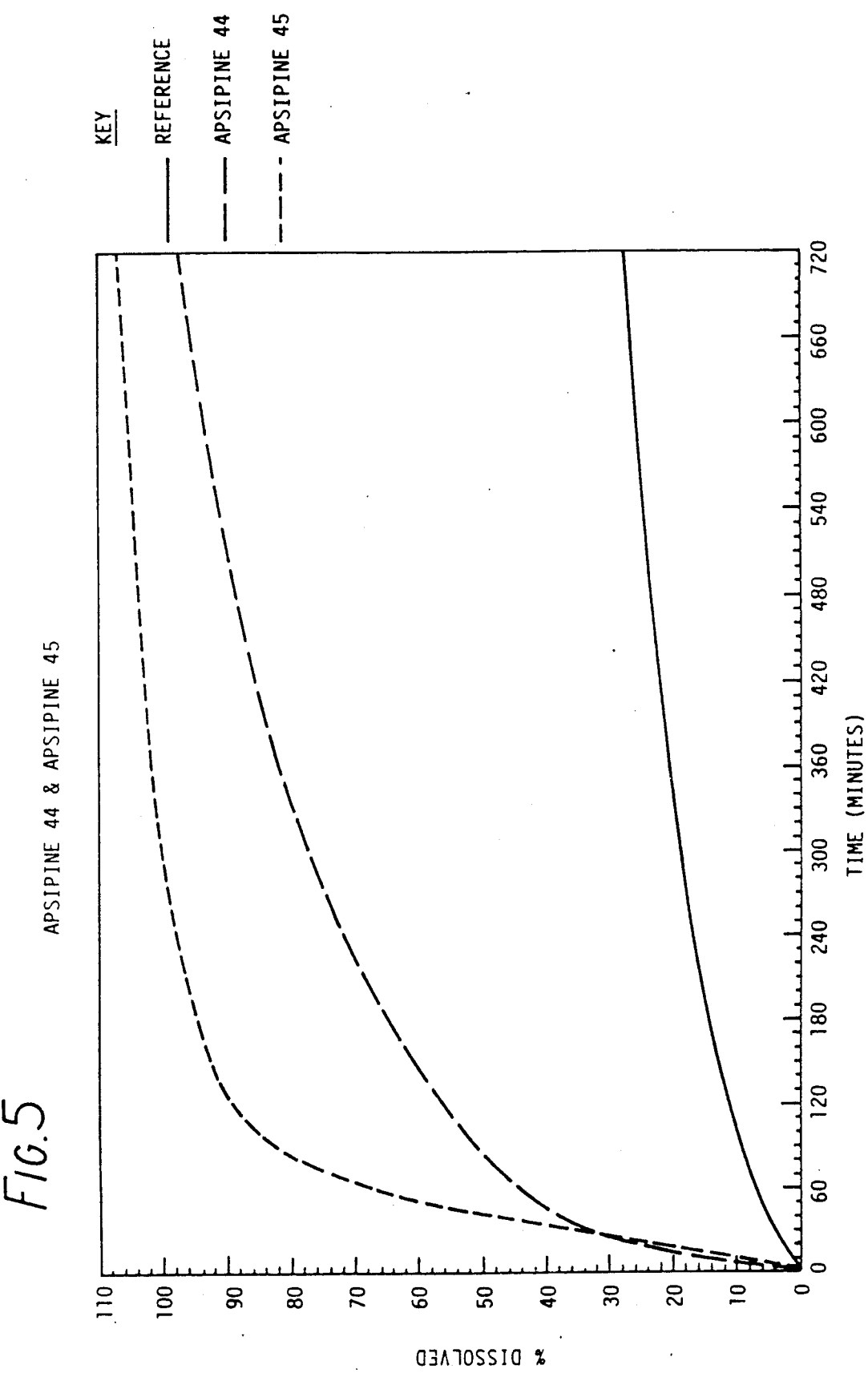

Dissolution tests were performed on samples of granules of the formulations and the results are shown in FIG. 5. The dissolution profiles show that the rate of nifedipine dissolution was greater in the granules in which the acid was added in solution (Apsipine 45) than in the other preparation (Apsipine 44).

EXAMPLE 7

The formulation of Example 1 was prepared and the particles were then given a coating of Eudragit NE30D and hydroxypropylmethyl cellulose (with a solid ratio of 5:1.5). The resulting formulation of the present invention was designated Apsipine 33/5.

The granules were rotated in a small coating pan and the coating mixture was added in portions to the pan until the weight of solids in the added coating mixture was 5% of the weight of the granules. After each portionwise addition of coating mixture, air was blown into the pan to assist in water removal. At the end of the addition of the coating mixture, the coated granules were dried to constant weight and sieved to produce coated granules having a size between 0.8 and 1.2 mm. A reference formulation was prepared as in Example 1 for comparative purposes.

Figure 6:
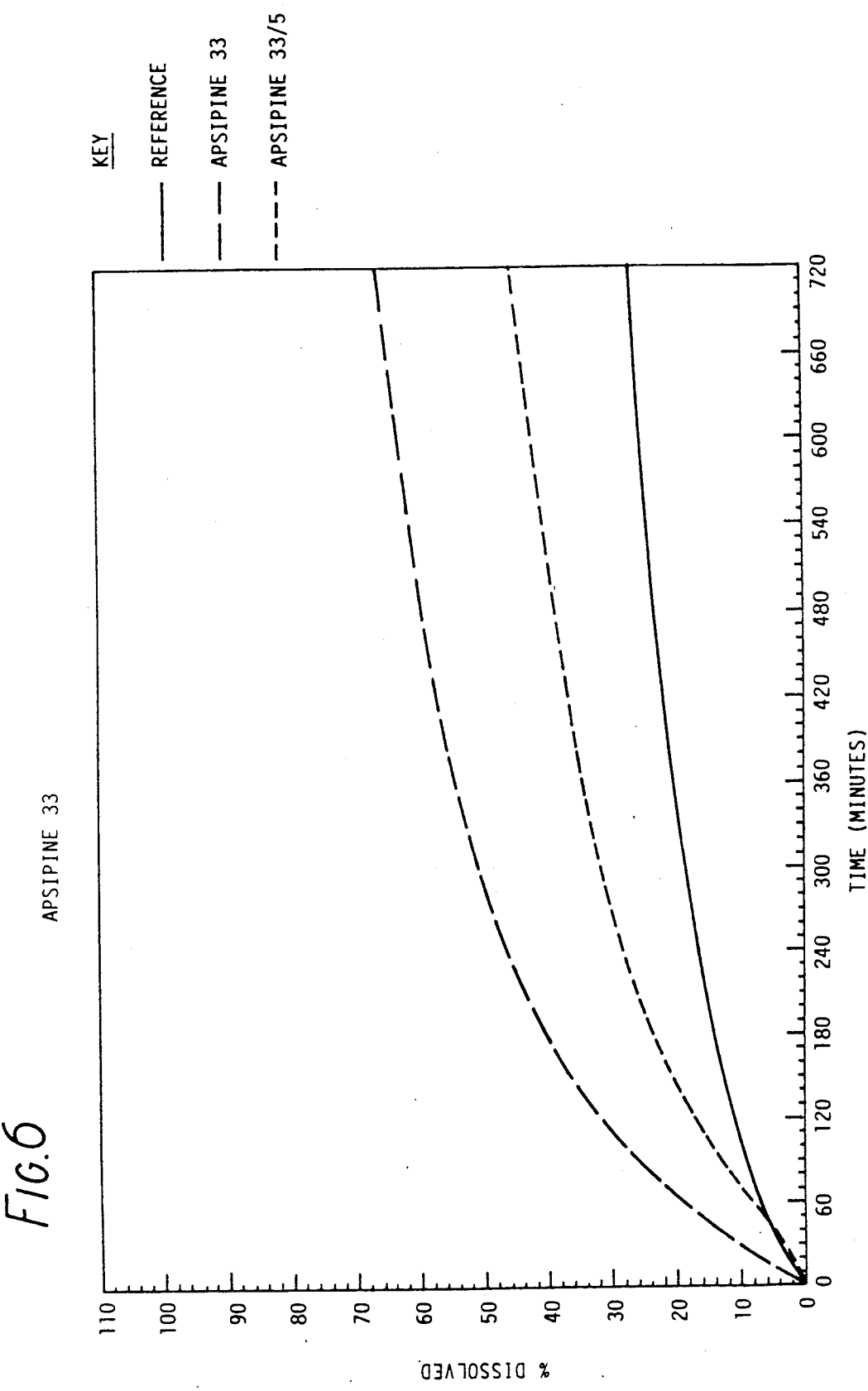

Dissolution tests were performed on samples of granules of both formulations and also on an identical but uncoated formulation of the present invention (Apsipine 33). The resulting dissolution profiles are shown in FIG. 6. The results show that the coating slowed the rate of release and produced an improved profile.

EXAMPLE 8

A formulation according to the present invention was prepared from the following components:
7% micronized nifedipine (surface area
3.0 m²/g)
14% Carbopol 934P
79% Avicel PH 101
0.1N hydrochloric acid to bind
The granules were prepared as in Example 1 and a coating of the same composition as in Example 7 applied until the weight of solids in the added coating mixture was 10% of the weight of the granules.

Figure 7:
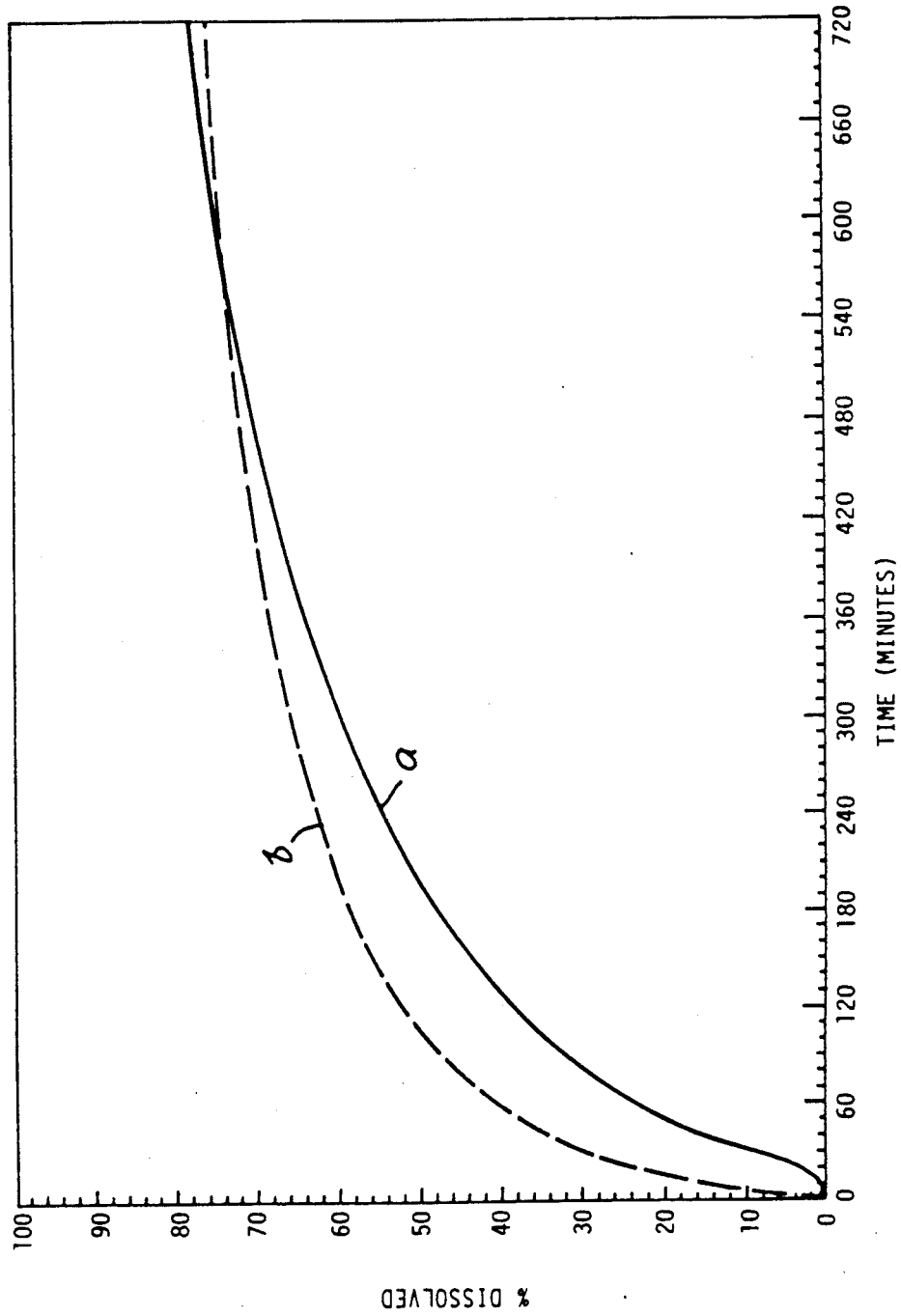

In vitro experiments were then carried out to determine the release properties of this formulation in comparison to the commercially available sustained-release product known as Adalat Retard. The dissolution test used was the USP basket method, pH 6.8, flat-bottomed flask, temperature of 37° C., detector wavelength 238 nm, optical density of 3 mg/l nifedipine solution = 0.171. The results are shown in FIG. 7.

The drug release profile for the formulation of this invention is superior to that obtained for Adalat Retard. This is because drug release over the first four hours is slower, reducing the potential for high initial plasma levels and associated clinical side effects—the formulation of the present invention releases 20% drug in one hour, 40% in two hours, whilst comparative figures for Adalat Retard tablets are 40% and 52% respectively. Between four and twelve hours, a preferred profile for the formulation of the present invention is also observed with nifedipine continuing to be released as the curve approaches and crosses the almost horizontal, minimally releasing profile of the Adalat Retard tablet. The superior drug release profile is attributed to the solubility enhancing feature of the carbomer for the poorly aqueous soluble nifedipine, thus creating a saturated nifedipine solution within the pores of the granule on dissolution, coupled to the action of the polymer coating.

EXAMPLE 9

A formulation according to the present invention was prepared from the following components:
5% Spironolactone
10% Carbopol 934P
85% Avicel PH 101/Lactose BP Mixture (9:1)
with distilled water to bind.

The spironolactone and an equal amount of Carbopol were ground together in a glass pestle and mortar. Using the "doubling-up" method the remaining components were added to the mixture. Water was added in portions until a slightly cohesive product was formed. The cohesive product was pressed into a perspex mould consisting of 100 holes of 2 mm diameter and 2 mm depth. The granules thus formed were dried to constant weight and then expressed from the mould. A reference formulation was prepared in a similar manner for comparative purposes, but with the 10% Carbopol replaced by a 10% lactose/Avicel mixture.

The dissolution test used was the USP basket method. The dissolution medium was buffer pH 7.4+4% ethanol at a temperature of 37° C. Detector wavelength was set at 244 nm and the optical density of 4 mg/l spironolactone solution was 0.173.

Figure 8:
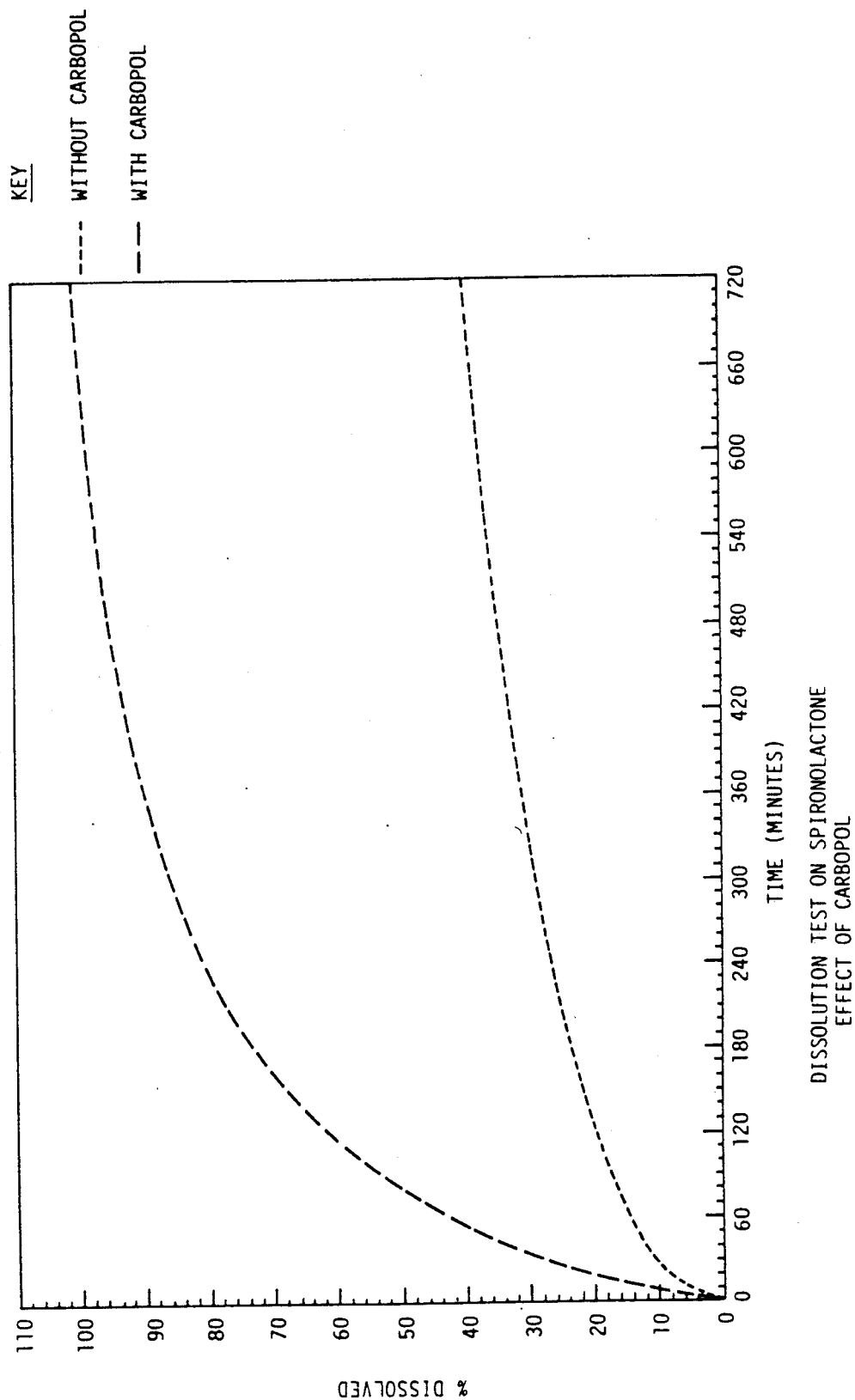

Dissolution tests were performed on samples of granules of both formulations and the results are shown in FIG. 8. The formulation of the present invention gave good sustained release over 12 hours and was complete at 100%, whereas the reference formulation only gave a 40% release after 12 hours.

EXAMPLE 10

A formulation according to the present invention was prepared from the following components:
5% Griseofulvin
10% Carbopol 934P
85% Avicel PH101/Lactose BP Mixture (9:1)
with distilled water to bind.

The griseofulvin and an equal amount of Carbopol were ground together in a glass pestle and mortar. Using the "doubling-up" method the remaining components were added to the mixture. Water was added in portions until a cohesive product was formed. The adhesive product was pressed into a perspex mould, consisting of 100 holes of 2 mm diameter and 2 mm depth. The granules thus formed were dried to constant weight and then expressed from the mould. A reference formulation was prepared in a similar manner for comparative purposes, but with the 10% Carbopol replaced by a 10% lactose/Avicel mixture.

The dissolution test used was the USP basket method. Dissolution medium was buffer pH 6.8 or buffer pH. 6.8+10% ethanol at a temperature of 37° C. Detector wavelength was set at 296 nm and the optical density 10 mg/l griseofulvin solution was 0.834.

Figure 9:
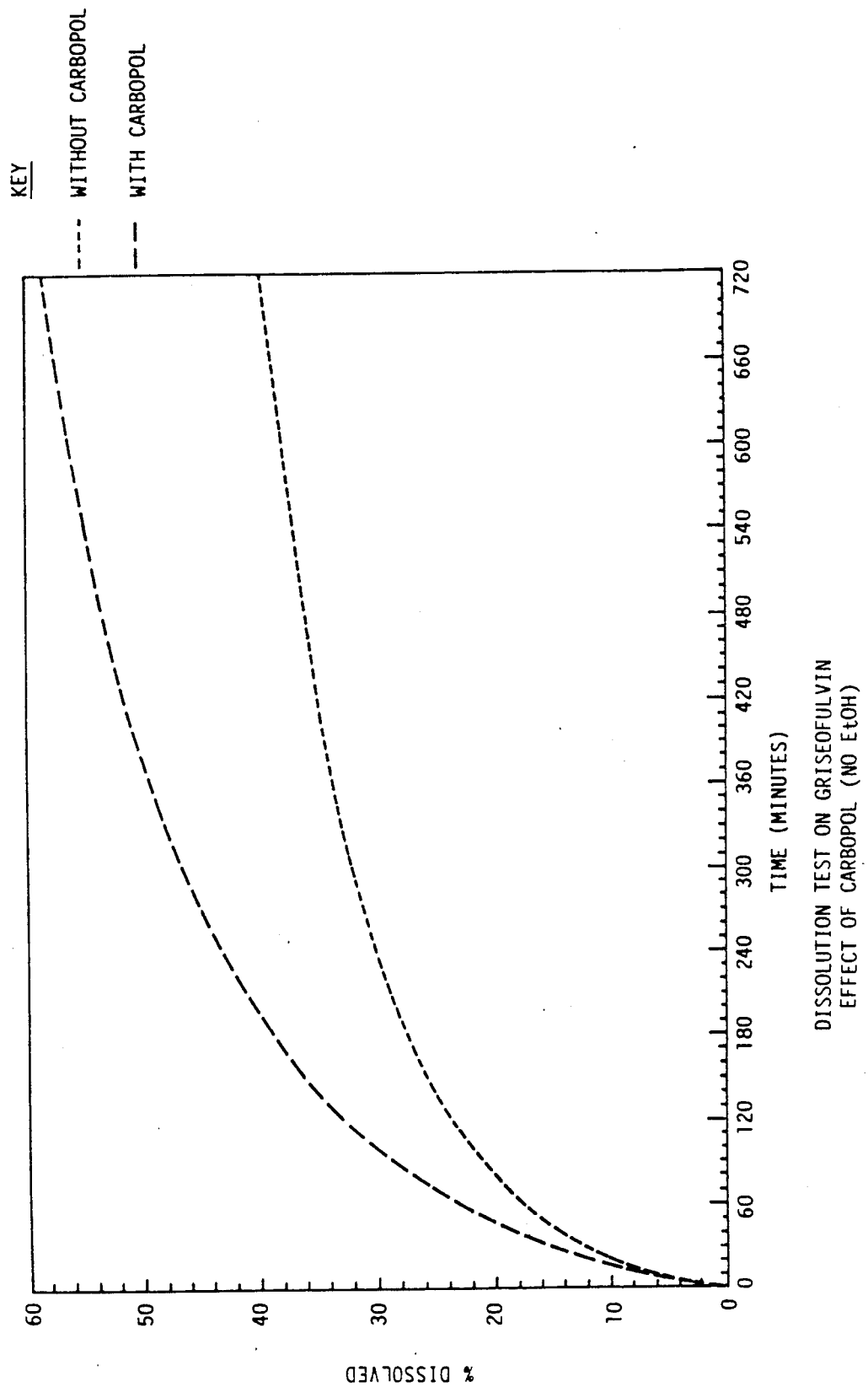

Dissolution tests were performed on samples of granules of both formulations and the results are shown in FIGS. 9 and 10. The formulation of the present invention in buffer pH 6.8+10% ethanol gave good release for 3–4 hours after which time the release rate slowed to give an 80% release after 12 hours, whereas the reference formulation gave a 55% release after 12 hours.

In buffer without ethanol in the dissolution medium the formulation gave good release for 3–4 hours after which time the release rate slowed to give 60% release after 12 hours, whereas the reference formulation gave a 40% release after 12 hours.

EXAMPLE 11

A formulation according to the present invention was prepared from the following components:
5% Glibenclamide
10% Carbopol 934P
85% Avicel PH101/Lactose BP Mixture (9:1)
with distilled water to bind.

The glibenclamide and an equal amount of Carbopol were ground together in a glass pestel and mortar. Using the "doubling-up" method the remaining components were added to the mixture. Water was added in portions until a slightly cohesive product was formed. The cohesive product was pressed into a perspex mould consisting of 100 holes of 2 mm diameter and 2 mm depth. The granules thus formed were dried to constant weight and then expressed from the mould.

The dissolution test used was the USP basket method. The dissolution medium was buffer pH 6.8+5% ethanol at a temperature of 37° C. Detector wavelength was set at 230 nm and the optical density at 5 mg/l glibenclamide solution was 0.326.

Dissoution tests were performed on samples of granules of both formulations and the results are shown in FIG. 11. The formulation of the present invention gave good release for 3–4 hours after which time the release rate slowed considerably to give over 60% release after 12 hours, whereas the reference formulation gave at release of only 30% after 12 hours.

It will be appreciated that the present invention has been described above by way of illustration only, and it will be clear that variations and alterations of detail may be made by the man skilled in the art without departing from the scope of the invention.

We claim:

1. A controlled-release formulation of a pharmacologically active substance of poor aqueous solubility comprising sufficient granules to provide a predetermined dose or number of doses of the pharmacologically active substance, each of said granules consisting essentially of 100 parts of said pharmacologically active substance and at least 20 parts of carbomer.

2. A controlled-release formulation of a pharmacologically active substance of poor aqueous solubility comprising sufficient granules to provide at least one predetermined dose of the pharmacologically active substance, each of said granules consisting essentially of about 100 parts of said pharmacologically active substance and at least about 20 parts of carbomer and each of the granules being provided with a coating covering substantially the whole surface thereof and comprising 100 parts of a water insoluble but water swellable acrylic polymer and from 20 to 70 parts of a water soluble hydroxylated cellulose derivative, the weight of the coating being from 2 to 25% of the weight of the underlying granule and the diameter of the coated granules being between 0.5 and 2.5 mm.

3. A controlled-release formulation of a pharmacologically active substance of poor aqueous solubility comprising sufficient granules to provide at least one predetermined dose of the pharmacologically active substance, each of said granules consisting essentially of about 100 parts of said pharmacologically active substance and at least about 20 parts of carbomer and each of the granules being provided with a coating covering substantially the whole surface thereof and comprising 100 parts of a water insoluble but water swellable acrylic polymer and from 20 to 70 parts of a water soluble hydroxylated cellulose derivative, the weight of the coating being from 2 to 25% of the weight of the underlying granule and the diameter of the coated granules being between 0.5 and 2.5 mm, which provides sustained release over a period of 12 hours, said granules containing from 100 to 300 parts of carbomer, the diameter of the coated granules being between 0.7 and 1.2 mm, the coating contain from 20 to 40 parts of the water soluble hydroxylated cellulose derivative, and the weight of the coating being between 2 and 10% of the weight of the underlying granule.

4. A formulation as claimed in claim 1, wherein the pharmacologically active substance is nifedipine, spironolactone, griseofulvin or glibenclamide.

5. A formulation as claimed in claim 1, wherein each of said granules contains from 100 to 300 parts of carbomer.

6. A formulation as claimed in claim 2, wherein said coating contains 30 parts of the hydroxylated cellulose derivative and which is hydroxypropylmethyl cellulose having a degree of substitution of 28 to 30% of methoxy groups and 7 to 12% hydroxy groups.

7. A controlled-release formulation of a pharmacologically active substance of poor aqueous solubility comprising sufficient granules to provide at least one predetermined dose of the pharmacologically active substance, each of said granules consisting essentially of about 100 parts of said pharmacologically active substance, at least about 20 parts of carbomer and sodium chloride, tri-sodium citrate or citric acid.

8. A controlled-release formulation of a pharmacologically active substance of poor aqueous solubility comprising sufficient granules within a capsule to provide at least one predetermined dose of the pharmacologically active substance, each of said granules consisting essentially of about 100 parts of said pharmacologically active substance and at least about 20 parts of carbomer.

9. A method for preparing a controlled-release formulation of pharmacologically active substance of poor aqueous solubility and which comprises:
  i) mixing the pharmacologically active substance with carbomer.

ii) forming the mixture into granules consisting essentially of 100 parts of the pharmacologically active substance and at least 20 parts of carbomer; and optionally iii) forming a suspension comprising 100 parts of a water insoluble but water swellable acrylic polymer and from 20 to 70 parts of a water soluble hydroxylated cellulose derivative; and iv) coating the said granules with the said suspension to form coated granules having a diameter of between 0.5 and 2.5 mm.

10. A method for preparing a controlled-release formulation of pharmacologically active substance of poor aqueous solubility and which comprises:

i) mixing the pharmacologically active substance with carbomer;

ii) forming the mixture into granules consisting essentially of 100 parts of the pharmacologically active substance and at least 20 parts of carbomer; and optionally iii) forming a suspension comprising 100 parts of a water insoluble but water swellable acrylic polymer and from 20 to 70 parts of a water soluble hydroxylated cellulose derivative;

iv) coating the said granules with the said suspension to form coated granules having a diameter of between 0.5 and 2.5 mm, and v) sieving the coated granules.

11. A method of treatment of the human or animal body and which comprises administering a controlled-release formulation as claimed in claim 1.

12. The controlled-release formulation as set forth in claim 2, including at least one excipient selected from the group consisting of a bulking agent, a diluent, and a capillary-active agent.

13. The controlled-release formulation as set forth in claim 3, including at least one excipient selected from the group consisting of a bulking agent, a diluent, and a capillary-active agent.

14. The controlled-release formulation as set forth in claim 7, including at least one excipient selected from the group consisting of a bulking agent, a diluent, and a capillary-active agent.

15. The controlled-release formulation as set forth in claim 8, including at least one excipient selected from the group consisting of a bulking agent, a diluent, and a capillary-active agent.

16. The controlled-release formulation as set forth in claim 10, including at least one excipient selected from the group consisting of a bulking agent, a diluent, and a capillary-active agent.

* * * * *

UNITED STATES PATENT AND TRADEMARK OFFICE
CERTIFICATE OF CORRECTION

PATENT NO. : 5,051,263
DATED : September 24, 1991
INVENTOR(S) : Brian W. BARRY; Bryan Arthur MULLEY; and Peter YORK It is certified that error appears in the above-identified patent and that said Letters Patent is hereby corrected as shown below:

Please correct the title page, insert --

[73] Assignee: APS Research Limited

Cleckheaton, Great Britain -- and insert after "Assistant Examiner-William E. Benston, Jr."

-- Attorney, Agent or Firm - Spencer & Frank --.

Signed and Sealed this

Sixteenth Day of March, 1993

*Attest:*

STEPHEN G. KUNIN

*Attesting Officer*      *Acting Commissioner of Patents and Trademarks*